United States Patent [19]
Fagan et al.

[11] Patent Number: 6,137,012
[45] Date of Patent: Oct. 24, 2000

[54] PHOSPHOLE AND DIPHOSPHOLE LIGANDS FOR CATALYSIS

[75] Inventors: Paul J. Fagan; George Yanwu Li, both of Wilmington; Zhibin Guan; Lin Wang, both of Hockessin, all of Del.

[73] Assignee: E. I. du Pont de Nemours and Company, Wilmington, Del.

[21] Appl. No.: 09/415,388

[22] Filed: Oct. 8, 1999

Related U.S. Application Data

[60] Provisional application No. 60/104,112, Oct. 13, 1998.

[51] Int. Cl.$^7$ ...................................................... C07F 9/50
[52] U.S. Cl. ................................. 568/12; 564/12
[58] Field of Search ................................. 568/12; 564/12

[56] References Cited

U.S. PATENT DOCUMENTS

| | | | |
|---|---|---|---|
| 2,577,208 | 12/1951 | Reppe et al. | 260/406 |
| 4,818,810 | 4/1989 | Drent | 528/391 |
| 4,835,250 | 5/1989 | Drent | 528/392 |

FOREIGN PATENT DOCUMENTS

WO 96/30421  10/1996  WIPO .

OTHER PUBLICATIONS

CA:121:57586 abs of Phosphorus, Sulfur Silicon and Relat Elem by Brunet et al 85(1–4) pp 207–215, 1993.
CA:109:73592 abs of J Organomet Chem by Deschamp et al 332(1–2) pp 141–152, 1987.
Schenk, W. A., "Reaktive Arsen–Heterocyclen", *Journal of Organometallic Chemistry*, vol. 467, No. 1, 67–73, 1994.
Doherty, S. et al., "Palladium Complexes of C2–, C3–, and C4–Bridged Bis(phospholyl) Ligands: Remarkably Active Catalysts for the Copolymerization of Ethylene and Carbon Monoxide", *Organometallics,* vol. 18, 3558–3560, 1999.
Kato et al.,, Macromolecules , 28, 1721, 1995.
Wang et al., Macromolecules , 28, 7572, 1995.
Wang et al., , Macromolecules , 28, 7901, 1995.
Drent et al., Chem. Rev., 1996, 96 663.
Bhaduri et al., Organometallics 1992, 11, pp. 4069–4076.
Quin, Compr. Heterocycl. Chem. II Bird, Clive W. (Ed), 1996, vol. 2, pp. 757–856.
Charrier et al., Organometallics 1987, 6 pp. 586 91.
Gradoz et al., J. Chem. Soc. Dalton Trans. 1992, pp. 3047–3051.
Fagan et al., J. Am. Chem. Soc. 1994, 116, pp. 1880–1889.
Fagan et al., J. Am. Chem. Soc. 1988, 110, pp. 2310–2312.
Neilbecker et al, New J. Chem. 1991, pp. 279–281.
Neilbecker et al., J. Mol. Catal. 1989, 57, pp. 153–163.
Neilbecker et al., J. Mol. Catal. 1989, 219–227.
Vac et al., Inorg. Chem. 1989 28, pp. 3831–3836.
Hjortkjaer et al., J. Mol. Catal. 1989 50, 203–210.
Gouygou et al., Organometallics 1997, 16, 1008–1015.
Granel et al., , Macromolecules , 29, 8576, 1996.
Brubaker, J. Am. Chem. Soc., 74, 1509, 1952.
Steinberg, Polym. Eng. Sci., 17, 335, 1977.

*Primary Examiner*—Jean F Vollano

[57] ABSTRACT

Novel reactions used to prepare phosphole and bisphosphole compounds are detailed. Novel phosphole compounds and metal coordination compounds of phosphole and bisphosphole compounds are also provided. These metal coordination compounds are useful as catalysts for the polymerization or olefins with carbon monoxide and for the polymerization of acrylic monomers.

4 Claims, No Drawings

PHOSPHOLE AND DIPHOSPHOLE LIGANDS FOR CATALYSIS

This application claims benefit of Provisional Application No. 60/104,112, filed Oct. 13, 1998.

FIELD OF INVENTION

The invention relates to new phosphole and diphosphole based ligands useful as polymerization catalysts.

BACKGROUND

The phosphole ring system is described by structure A. This structure is distinct from the class of compounds B which contain benzo rings fused to the phosphole core.

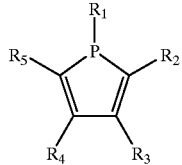

A

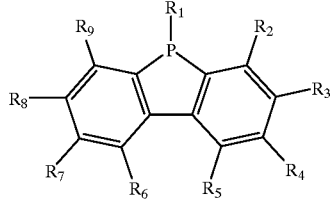

B

Class I has a much different electronic structure and therefore has much different chemistry than compounds of class II. In class I, the P atom is part of the delocalized, partially aromatic ring system. In class II, the aromaticity is confined to the benzo rings, with no delocalization around the P atom. Class I will participate in Diels-Alder chemistry (especially when complexed to a metal) (Bhaduri et al., *Organometallics* 1992, 11, pp. 4069–4076), whereas compounds of class II will not (Quin, *Compr. Heterocycl. Chem. II* Bird, Clive W (Ed), 1996, Vol. 2, pp. 757–856).

Very few compounds have been reported that contain two phosphole rings connected via a bridge (A) between the phosphorus atoms (structure C) (A=bridging hydrocarbon, hydrocarbon/heteroatom(s), or organometallic group).

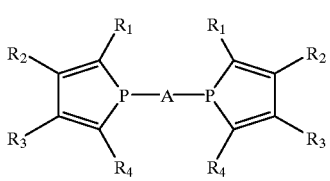

G

One explanation for the paucity of compounds of type C-G is the lack of synthetic procedures broad enough in scope to prepare the phosphole ring system.

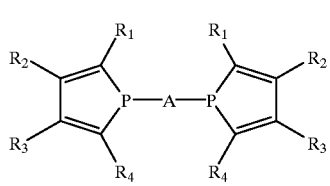

C

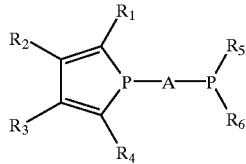

D

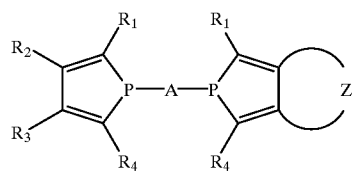

E

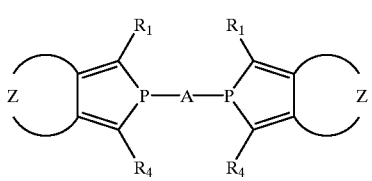

F

Examples reported in the literature include the compounds 1 (Braye et al., *Tetrahedron* 1971, pp. 5523–37), 2 (A=—CH$_2$—, —CH$_2$CH$_2$—, and —CH=CH—CH=CH—) (Charrier et al., *Organometallics* 1987, 6 pp. 586 91), and 3 (Gradoz et al., *J. Chem. Soc. Dalton Trans.* 1992, pp. 3047–3051).

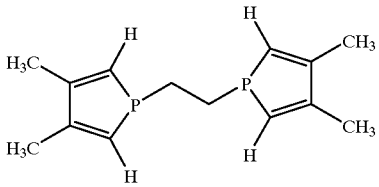

1

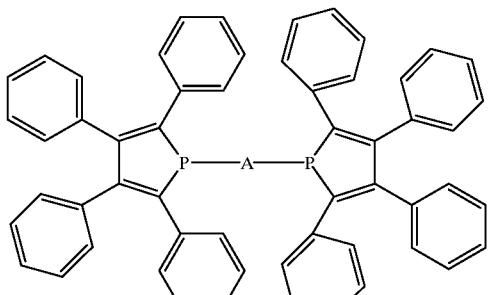

2

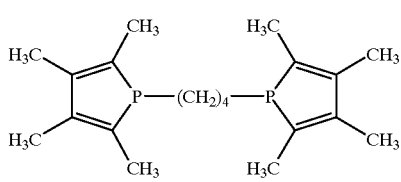

3

Compounds containing a single phosphole ring (I) were made using the Fagan-Nugent heterocycle synthesis (Fagan et al., *J. Am. Chem. Soc.* 1994, 116, pp. 1880–1889; Fagan et al., *J. Am. Chem. Soc.* 1988, 110, pp. 2310–2312). This synthesis involves preparing the zirconium reagents by coupling of acetylenes followed by transfer of the metallacycle from zirconium to phosphorus. In all cases, the substituent on the phosphorus was an aromatic group such as phenyl.

These types of compounds (containing a single phosphole ring) have found limited utility as ligands for transition metals for use in catalysis, and have been shown to have different chemistries than their phosphine analogs (Neibecker et al., *New J. Chem.* 1991, pp. 279–81; Neibecker et al., *J. Mol. Catal.* 1989, 57 pp. 153–163; Neibecker et al., *J. Mol. Catal.* 1989, 219–227; Vac et al., *Inorg. Chem.* 1989 28, pp. 3831–3836; Hjortkjaer et al., *J. Mol. Catal.* 1989 50, 203–210).

Transition metal complexes have been made using structures of class VII, shown below, where the rings are linked at the position alpha to phosphorus. Attempts to use these ligands to make Pd acetonitrile complexes analogous to those in the instant invention failed (Guoygou et al., *Organometallics* 1997, 16, 1008–1015).

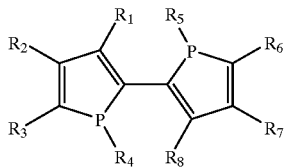

G

Copolymers of carbon monoxide and olefins, such as ethylene, can be made by free radical initiated copolymerization (Brubaker, *J. Am. Chem. Soc.*, 1952, 74, 1509) or gamma-ray induced copolymerization (Steinberg, *Polym. Eng. Sci.*, 1977, 17, 335). The copolymers produced were random copolymers and their melting points were low. In 1951, Reppe discovered a nickel-catalyzed ethylene carbon monoxide copolymerization system that gave alternating copolymers (U.S. Pat. No. 2,577,208 (1951)). However, the molecular weights of these polymers were also low.

In 1984, U.S. Pat. Nos. 4,818,810 and 4,835,250 disclosed the production of alternating olefin carbon monoxide copolymers based on Pd(II), Ni(II) and Co(II) complexes bearing bidentate ligands of the formula $R_1R_2E$—A—E—$R_3R_4$, wherein $R_1$, $R_2$, $R_3$, $R_4$, and A are organic groups and E is phosphorus, arsenic, or antimony. When E is phosphorus and $R_{1-4}$ are aryl groups, the corresponding diphosphine palladium complexes are active in copolymerizing ethylene and carbon monoxide to produce copolymers of molecular weight up to 30,000 ($MW_n$) (Drent et al., *Chem. Rev.*, 1996, 96, 663). No compounds were claimed or disclosed in which $R_1$ and $R_2$, and $R_3$ and $R_4$ together formed a ring. Applicants have recently found that the diphosphole coordinated palladium catalysts catalyze olefin/carbon monoxide (CO) copolymerization. When the P atom is part of a ring system, the electronic environment and therefore expected chemistries are different than simple, non-ring phosphine disclosed in the patents described above.

Radical polymerization is an important commercial process for making a variety of polymers of vinyl monomers, such as acrylics and styrenics. While this process makes large amounts of polymers, the difficulty in accurately controlling the polymer structures (such as molecular weight, molecular weight distribution, and architecture, etc.) has significantly limited its further applications.

Living polymerization usually offers much better control on polymer structures and architectures. While living polymerization systems for anionic, cationic, and group transfer mechanisms were developed some years ago, a true living radical polymerization system is still an elusive goal (because of the high reactivity of free radicals) and only very recently has pseudo-living radical polymerization been achieved. One pseudo-living radical polymerization method is "atom transfer radical polymerization" (ATRP). In this process a transition metal compound, usually in a lower valent state, is contacted with a compound which is capable of transferring an atom to the metal complex, thereby oxidizing the metal to a higher valent state and forming a radical which can initiate polymerization. However, the atom that was transferred to the metal complex may be reversibly transferred back to the growing polymer chain at any time. In this way, the propagation step is regulated by this reversible atom transfer equilibrium and statistically all polymer chains grow at the same rate. The results a pseudo-living radical polymerization in which the molecular weight may be closely controlled and the molecular weight distribution is narrow.

Such ATRPs are described in many publications (Kato et al., *Macromolecules* 1995, 28, 1721; Wang et al., *Macromolecules* 1995, 28, 7572; Wang et al., *Macromolecules* 1995, 28, 7901; Granel et al., *Macromolecules* 1996, 29, 8576; Matyjaszewski et al., PCT WO 96/30421). The transition metal complexes used include complexes of Cu(I), Ru(II), Ni(II), Fe(II), and Rh(II). The complexes are formed by coordinating the metal ions with certain ligands such as nitrogen or phosphine containing ligands. For Ru(II) and Fe(II), mono-phosphine $P(C_6H_5)_3$ was used as the ligand. However, for Cu(I), all the ligands used are nitrogen-based such as bipyridine or substituted bipyridine. No phosphine-based ligand has been shown to be an effective ligand for Cu(I) in ATRP.

It has been found that novel types of ligands containing phosphole and other P ring systems can chelate Cu(I) to form active catalysts for ATRP.

SUMMARY OF THE INVENTION

An object of this invention is to provide a process for the preparation of compounds of formulae I and II

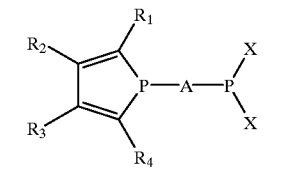

I

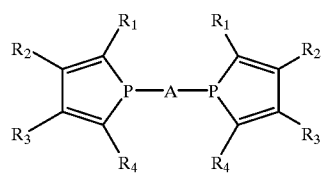

II by reacting a compound of formula $X_2P$—A—$PX_2$ (III) with a compound of formula IV;

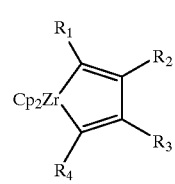

IV wherein $R_1$, $R_2$, $R_3$ and $R_4$ are independently selected from the group consisting of hydrogen, hydrocarbyl, and substituted hydrocarbyl; $R_2$ and $R_3$ together can optionally form a ring; Cp is cyclopentadienyl; X is selected from the group consisting of Cl, Br, and I; A is a divalent group consisting of optionally-subsituted chains of from 1 to 12 linear, branched, or cyclic carbons, optionally containing one or more heteroatoms or organometallic groups in the chain, and —N(R$_7$)—N(R$_8$)—; and R$_7$ and R$_8$ are independently selected from the group consisting of hydrogen, hydrocarbyl, and substituted hydrocarbyl.

Preferably A is selected from the group consisting of a carbon chain of 1–3 carbons and —N(R$_7$)—N(R$_8$)—, wherein R$_7$ and R$_8$ are independently selected from the group consisting of hydrogen, hydrocarbyl, and substituted hydrocarbyl. More preferably R$_1$, R$_2$, R$_3$ and R$_4$ are alkyl groups.

The invention also provides for a compound of the formula

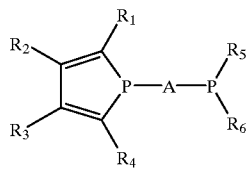

V wherein R$_1$, R$_2$, R$_3$ and R$_4$ are independently selected from the group consisting of hydrogen, hydrocarbyl, and substituted hydrocarbyl; R$_5$ and R$_6$ are independently selected from the group consisting of hydrogen, hydrocarbyl, substituted hydrocarbyl, Cl, Br, I , N, O and S; R$_2$ and R$_3$ together and R$_5$ and R$_6$ together can optionally form a ring; Cp is cyclopentadienyl ($\eta^5$—C$_5$H$_5$); A is a divalent group consisting of optionally-substituted chains of from 1 to 12 linear, branched, or cyclic carbons, optionally containing one or more heteroatoms or organometallic groups in the chain, and —N(R$_7$)—N(R$_8$)—; and R$_7$ and R$_8$ are independently selected from the group consisting of hydrogen, hydrocarbyl, and substituted hydrocarbyl.

Preferably A is selected from the group consisting of a carbon chain of 1–3 carbons and —N(R$_7$)—N(R$_8$)—, wherein R$_7$ and R$_8$ are independently selected from the group consisting of hydrogen, hydrocarbyl, and substituted hydrocarbyl. More preferably R$_1$, R$_2$, R$_3$ and R$_4$ are alkyl groups and R$_5$ and R$_6$ are selected from the group consisting of alkyl groups and Cl.

A further object of the invention is a coordination compound comprising one or more transition metals complexed to one or more of the following compounds as ligands:

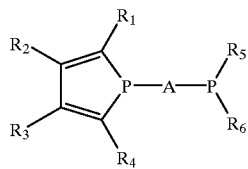

V

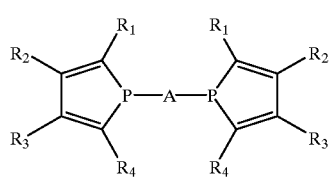

II wherein R$_1$, R$_2$, R$_3$ and R$_4$ are independently selected from the group consisting of hydrogen, hydrocarbyl, and substituted hydrocarbyl; R$_5$ and R$_6$ are independently selected from the group consisting of hydrogen, hydrocarbyl, substituted hydrocarbyl, Cl, Br, I, N, O and S; R$_2$ and R$_3$ together and R$_5$ and R$_6$ together can optionally form a ring; A is a divalent group consisting of optionally-substituted chains of from 1 to 12 linear, branched, or cyclic carbons, optionally containing one or more heteroatoms or organometallic groups in the chain, and —N(R$_7$)—N(R$_8$)—; and R$_7$ and R$_8$ are independently selected from the group consisting of hydrogen, hydrocarbyl, and substituted hydrocarbyl.

Preferably the transition metal is Pd and A is selected from the group consisting of a carbon chain of 1–3 carbons and —N(R$_7$)—N(R$_8$)—, wherein R$_7$ and R$_8$ are independently selected from the group consisting of hydrogen, hydrocarbyl, and substituted hydrocarbyl. More preferably R$_1$, R$_2$, R$_3$, and R$_4$ are alkyl groups and R$_5$ and R$_6$ are selected from the group consisting of alkyl groups and Cl.

The invention also provides a process for the preparation of a polyketone by contacting a mixture of carbon monoxide with one or more alkenes under polymerization conditions with a catalyst comprising a transition metal complexed with one or more ligands of the formulae IIA or VA

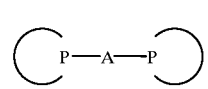

IIA

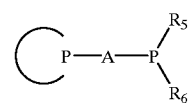

VA wherein the rings are optionally-substituted and are optionally members of a larger bicyclic or tricyclic ring system; each P atom is bonded to only three other atoms in the ligand; the two atoms in the ring adjacent to the P atom are C atoms; R$_5$ and R$_6$ are independently selected from the group consisting of hydrogen, hydrocarbyl, substituted hydrocarbyl, Cl, Br, I, N, O, and S; R$_5$ and R$_6$ together can optionally form a ring; A is a divalent group consisting of optionally-substituted chains of from 1 to 12 linear, branched, or cyclic carbons, optionally containing one or more heteroatoms or organometallic groups in the chain, and —N(R$_7$)—N(R$_8$)—; and R$_7$ and R$_8$ are independently selected from the group consisting of hydrogen, hydrocarbyl, and substituted hydrocarbyl.

Preferably the transition metal is Pd and the ligand is of the formulae V or II

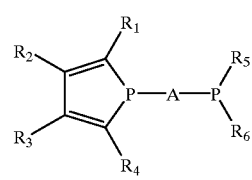

V

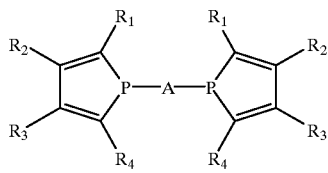

II wherein R, $R_2$, $R_3$, and $R_4$ are independently selected from the group consisting of hydrogen, hydrocarbyl, and substituted hydrocarbyl; $R_5$ and $R_6$ are independently selected from the group consisting of hydrogen, hydrocarbyl, substituted hydrocarbyl, Cl, Br, I, N, O, and S; $R_2$ and $R_3$ together and $R_5$ and $R_6$ together can optionally form a ring; A is a divalent group consisting of optionally-substituted chains of from 1 to 12 linear, branched, or cyclic carbons, optionally containing one or more heteroatoms or organometallic groups in the chain, and —N($R_7$)—N($R_8$)—; and $R_7$ and $R_8$ are independently selected from the group consisting of hydrogen, hydrocarbyl, and substituted hydrocarbyl. More preferably A is selected from the group consisting of a carbon chain of 1–3 carbons and —N($R_7$)—N($R_8$)—, $R_7$ and $R_8$ are independently selected from the group consisting of hydrogen, hydrocarbyl, and substituted hydrocarbyl $R_1$, $R_2$, $R_3$, and $R_4$ are alkyl groups, $R_5$ and $R_6$ are selected from the group consisting of alkyl groups and Cl, and the alkene is ethylene.

Another object of the invention is a process for the polymerization of an acrylic monomer by contacting at least one acrylic monomer under polymerization conditions with a catalyst comprising Cu(I) complexed with one or more ligands of the formulae IIA or VA

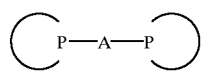

IIA

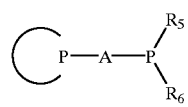

VA wherein the rings are optionally-substituted and are optionally members of a larger bicyclic or tricyclic ring system; each P atom is bonded to only three other atoms in the ligand; the two atoms in the ring adjacent to the P atom are C atoms; $R_5$ and $R_6$ are independently selected from the group consisting of hydrogen, hydrocarbyl, substituted hydrocarbyl, Cl, Br, I, N, O, and S; $R_5$ and $R_6$ together can optionally form a ring; A is a divalent group of optionally-substituted chains of from 1 to 12 linear, branched, or cyclic carbons, optionally containing one or more heteroatoms or organometallic groups in the chain, and —N($R_7$)—N($R_8$)—; and $R_7$ and $R_8$ are independently selected from the group consisting of hydrogen, hydrocarbyl, and substituted hydrocarbyl.

Preferably the ligand is of the formulae V or II

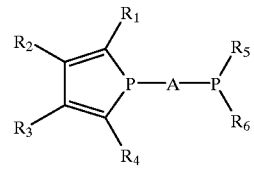

V

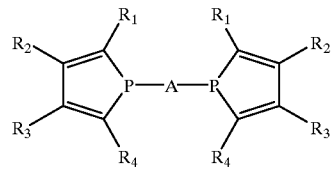

II wherein $R_1$, $R_2$, $R_3$, and $R_4$ are independently selected from the group consisting of hydrogen, hydrocarbyl, and substituted hydrocarbyl; $R_5$ and $R_6$ are independently selected from the group consisting of hydrogen, hydrocarbyl, substituted hydrocarbyl, Cl, Br, I, N, O, and S; $R_2$ and $R_3$ together and $R_5$ and $R_6$ together can optionally form a ring; A is a divalent group consisting of optionally-substituted chains of from 1 to 12 linear, branched, or cyclic carbons, optionally containing one or more heteroatoms or organometallic groups in the chain, and —N($R_7$)—N($R_8$)—; and $R_7$ and $R_8$ are independently selected from the group consisting of hydrogen, hydrocarbyl, and substituted hydrocarbyl. More preferably A is selected from the group consisting of a carbon chain of 1–3 carbons and —N($R_7$)—N($R_8$)—, wherein $R_7$ and $R_8$ are independently selected from the group consisting of hydrogen, hydrocarbyl, and substituted hydrocarbyl, $R_1$, $R_2$, $R_3$, and $R_4$ re alkyl groups, $R_5$ and $R_6$ are selected from the group consisting of alkyl groups and Cl, and the acrylic monomer is methylmethacrylate.

DETAILED DESCRIPTION OF THE INVENTION

This invention provides novel reactions used to prepare phosphole and bisphosphole compounds. Novel phosphole compounds and metal coordination compounds of phosphole and bisphosphole compounds are also provided. These metal coordination compounds are useful as polymerization catalysts.

The present invention provides processes for the preparation of bisphosphole compounds of formulae I and II

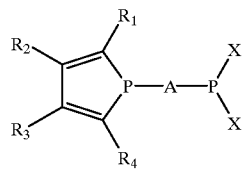

I

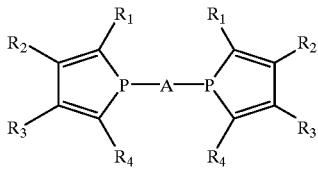

II by reacting a compound of formula IV with a compound of formula $X_2P$—A—$PX_2$ (III);

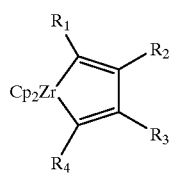

IV wherein:

$R_1$, $R_2$, $R_3$, and $R_4$ are independently selected from the group consisting of hydrogen, hydrocarbyl, and substituted hydrocarbyl;

$R_2$ and $R_3$ together can optionally form a ring;

Cp is cyclopentadienyl ($\eta^5$—$C_5H_5$);

X is selected from the group consisting of Cl, Br, and I;

A is a divalent group consisting of optionally-substituted chains of from 1 to 12 linear, branched, or cyclic carbons, optionally containing one or more heteroatoms or organometallic groups in the chain, and —N($R_7$)—N($R_8$)—; and $R_7$ and $R_8$ are independently selected from the group consisting of hydrogen, hydrocarbyl, and substituted hydrocarbyl.

By hydrocarbyl is meant a straight chain, branched or cyclic arrangement of carbon atoms connected by single, double, or triple carbon to carbon bonds and/or by ether linkages, and substituted accordingly with hydrogen atoms. Such hydrocarbyl groups may be aliphatic and/or aromatic. Examples of hydrocarbyl groups include methyl, ethyl, propyl, isopropyl, butyl, isobutyl, t-butyl, cyclopropyl, cyclobutyl, cyclopentyl, methylcyclopentyl, cyclohexyl, methylcyclohexyl, benzyl, phenyl, o-tolyl, m-tolyl, p-tolyl, xylyl, vinyl, allyl, butenyl, cyclohexenyl, cyclooctenyl, cyclooctadienyl, and butynyl. Examples of substituted hydrocarbyl groups include toluyl, chlorobenzyl, fluoroethyl, p-$CH_3$—S—$C_6H_5$, 2-methoxy-propyl, and $(CH_3)_3SiCH_2$—.

"Coordination compound" refers to a compound formed by the union of a metal ion (usually a transition metal) with a non-metallic ion or molecule called a ligand or complexing agent.

Preferred compounds of formulae II and I include those where A is selected from the group consisting of —N($R_7$)—N($R_8$)— and carbon chains of 1–3 carbons. Also preferred are compounds of formulae III and IV where $R_1$, $R_2$, $R_3$, and $R_4$ are alkyl groups. Most preferred are 1,2-bis(2,3,4,5-tetramethylphospholy)ethane; 1,2-bis(2,3,4,5-tetraethylphospholyl)ethane; 1,1-bis(2,3,4,5-tetramethylphospholy)methane; 1,1-bis(2,3,4,5-tetraethylphospholyl)methane; 1,2-bis(2,3,4,5-tetramethylphospholyl)-1,2-dimethylhydrazine; 1-(2,3,4,5-tetramethylphospholyl)-2-dichlorophosphinoethane; and 1-(2,3,4,5-tetramethylphospholyl)-2-dichlorophosphinoethane-1,2-dimethylhydrazine.

The process can be run in a wide variety of solvents. Preferred solvents are $CH_2Cl_2$ and THF (tetrahydrofuran). Low temperatures, below from about −100° C. to room temperature, are typically used.

The zirconium reagents (IV) are first prepared by reacting $Cp_2ZrCl_2$ (Cp=$\eta^5$—$C_5H_5$, cyclopentadienyl) with n-BuLi at about −78° C. followed by warming in the presence of an alkyne, alkynes, or dialkyne. The metallacycles can be isolated, or used in situ. When these are reacted with one-half of a molar equivalent of a diphosphorus compound $X_2P$—A—$PX_2$, compounds of formula II result (Scheme 1).

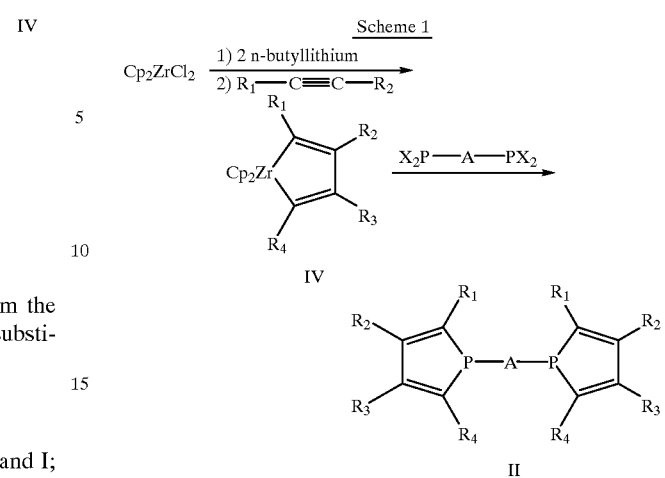

If zirconium metallacycles of type IV are reacted with at least one equivalent of the phosphorus reagents $X_2P$—A—$PX_2$, then compounds of formula I can be prepared (Scheme 2).

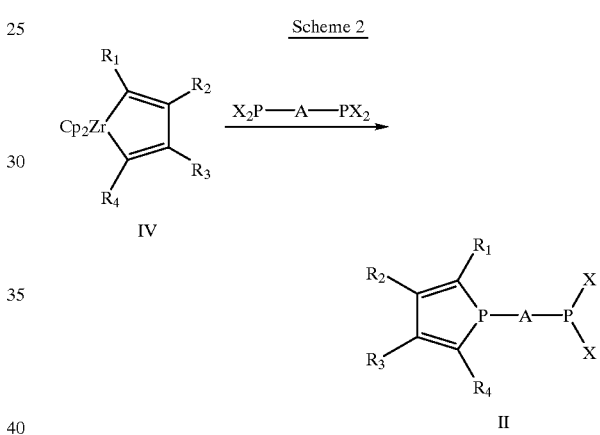

Dialkynes provide zirconium metallacycles of formula IVA which can be reacted with $X_2P$—A—$PX_2$ to form compounds of formula II wherein $R_2$ and $R_3$ together form a ring as illustrated in Scheme 3.

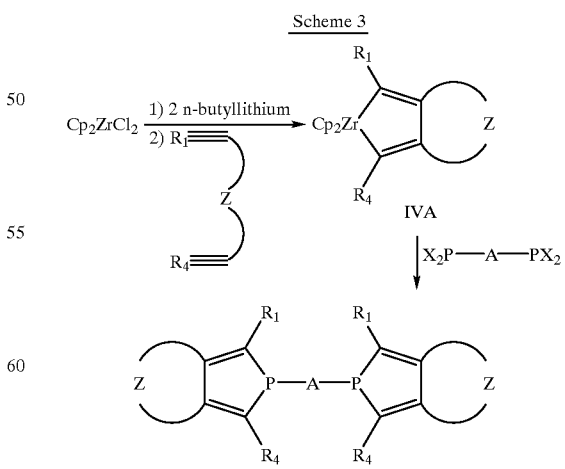

where Z is any linking group with proper orientation or is flexible enough to allow the reaction to proceed. Examples of suitable linking groups include hydrocarbyl, substituted hydrocarbyl, and organometallic compounds. Preferred is —(CH$_2$)$_x$—, where X is 1–10.

The above reactions should be performed under a N$_2$ atmosphere using anhydrous solvents.

Similarly, the products from reaction of zirconium metallacycles IVA allows the corresponding compounds of formula I wherein R$_2$ and R$_3$ together form a ring to be prepared (Scheme 4).

Scheme 4

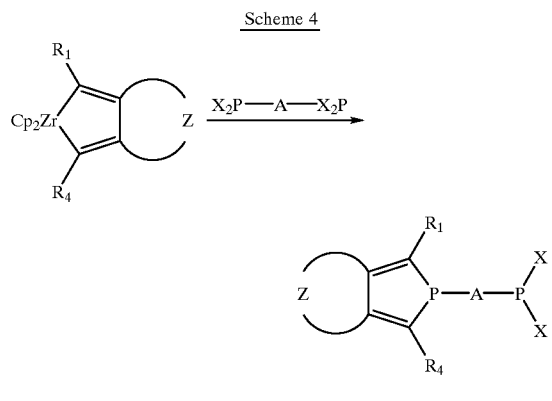

The present invention also provides for novel phosphole compositions of the formula V

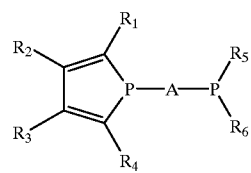

wherein

R$_1$, R$_2$, R$_3$, and R$_4$ are independently selected from the group consisting of hydrogen, hydrocarbyl, and substituted hydrocarbyl;

R$_5$ and R$_6$ are independently selected from the group consisting of hydrogen, hydrocarbyl, substituted hydrocarbyl, Cl, Br, I, N, O, and S;

R$_2$ and R$_3$ together and R$_5$ and R$_6$ together can optionally form a ring;

A is a divalent group consisting of optionally-substituted chains of from 1 to 12 linear, branched, or cyclic carbons, optionally containing one or more heteroatoms or organometallic groups in the chain, and —N(R$_7$)—N(R$_8$)—; and R$_7$ and R$_8$ are independently selected from the group consisting of hydrogen, hydrocarbyl, and substituted hydrocarbyl.

Preferred compounds of formulae V include those where A is selected from the group consisting of —N(R$_7$)—N(R$_8$)— and carbon chains of 1–3 carbons. Also preferred are compounds of formulae V where R$_1$, R$_2$, R$_3$, and R$_4$ are alkyl groups, and where R$_5$ and R$_6$ are hydrocarbyl, substituted hydrocarbyl, alkoxy, Cl, Br, and I. Most preferred are 1-(2,3,4,5-tetramethylphospholyl)-2-dichlorophosphinoethane; 1-(2,3,4,5-tetramethylphospholyl)-2-dichlorophosphinoethane-1,2-dimethylhydrazine; [2-(tetramethylphospholyl)ethyl]-[(R, R)-2,7-dimethyl-3,6-decadiyl]phosphine; 1-(2,3,4,5-tetramethylphospholyl)-2-di-(4-methylphenyl) phosphinoethane; 1-(2,3,4,5-tetramethylphospholyl)-2-di-(4-chlorophenyl)phosphinoethane; 1-(2,3,4,5-tetramethylphospholyl)-2-di-(4-tert-butylphenyl) phosphinoethane; 1-(2,3,4,5-tetramethylphospholyl)-2-diethynylphosphinoethane; 1-(2,3,4,5-tetramethylphospholyl)-2-di-(n-propynyl)phosphinoethane; 1-(2,3,4,5-tetramethylphospholy)-2-di-(4-fluorophenyl) phosphinoethane; 1-(2,3,4,5-tetramethylphospholyl)-2-di-(phenylethynyl)phosphinoethane; 1-(2,3,4,5-tetramethylphospholy)-2-divinylphosphinoethane; 1-(2,3,4,5-tetramethylphospholyl)-2-dicyclopentylphosphinoethane; 1-(2,3,4,5-tetramethylphospholyl)-2-di-(n-decyl) phosphinoethane; 1-(2,3,4,5-tetramethylphospholyl)-2-di-(4-fluoro-3-methylphenyl)phosphinoethane; 1-(2,3,4,5-tetramethylphospholyl)-2-di-(3,4-difluorophenyl) phosphinoethane; 1-(2,3,4,5-tetramethylphospholyl)-2-di-(4-butylphenyl)phosphinoethane; 1-(2,3,4,5-tetramethylphospholyl)-2-di-(3-fluoro-2-methylphenyl) phosphinoethane; 1-(2,3,4,5-tetramethylphospholyl)-2-di-(2-naphthyl)phosphinoethane; 1-(2,3,4,5-tetramethylphospholyl)-2-di-(4-methylthiophenyl) phosphinoethane; 1-(2,3,4,5-tetramethylphospholyl)-2-di-(3-methoxyphenyl)phosphinoethane; 1-(2,3,4,5-tetramethylphospholyl)-2-di-(3-fluoro-4-methylphenyl) phosphinoethane; 1-(2,3,4,5-tetramethylphospholyl)-2-di-(2-methoxyphenyl)phosphinoethane; 1-(2,3,4,5-tetramethylphospholyl)-2-di-(4-methoxphenyl) phosphinoethane; 1-(2,3,4,5-tetramethylphospholyl)-2-di-(4-phenoxyphenyl)phosphinoethane; 1-(2,3,4,5-tetramethylphospholyl)-2-di-[4-(dimethylamino)phenyl] phosphinoethane; 1-(2,3,4,5-tetramethylphospholyl)-2-di-(2,4-difluorophenyl)phosphinoethane; 1-(2,3,4,5-tetramethylphospholyl)-2-di-(2,4,6-trimethylphenyl) phosphinoethane; 1-(2,3,4,5-tetramethylphospholyl)-2-di-isopropenylphosphinoethane; 1-(2,3,4,5-tetramethylphospholyl)-2-diallyl-phosphinoethane; 1-(2,3,4,5-tetramethylphospholyl)-2-di-trimethylsilylmethylphosphinoethane; and 1-(2,3,4,5-tetramethylphospholyl)-2-di-[2-[1,3]dioxan-2-yl-ethyl] phosphinoethane.

Compounds of formula V where X is Cl, Br, or I can be prepared as detailed above. Other compounds of formula V can be prepared using compounds of formula I as an intermediate (Scheme 6).

Scheme 6

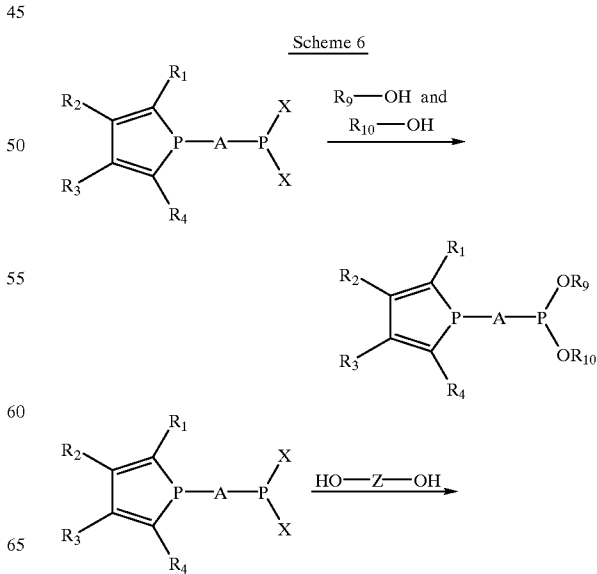

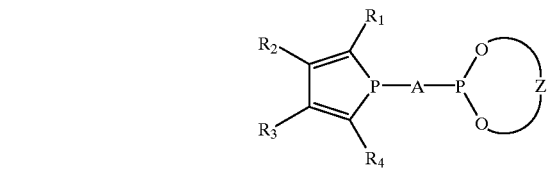

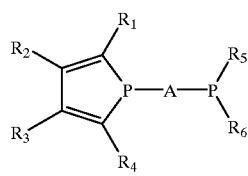

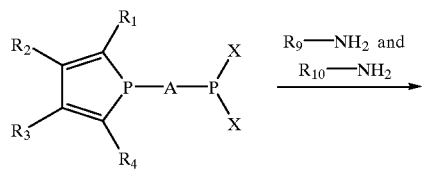

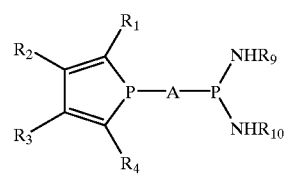

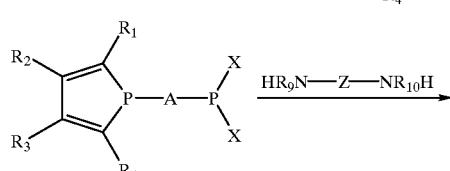

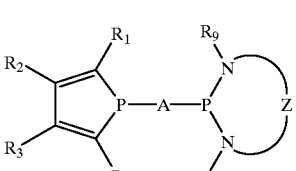

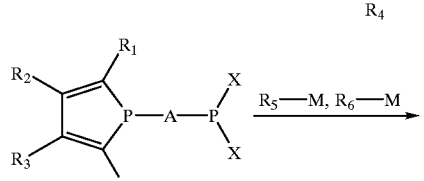

wherein $R_1$, $R_2$, $R_3$, $R_4$, $R_5$, $R_6$, $R_7$, $R_8$, A, and Z are as defined above, $R_9$ and $R_{10}$ are selected from the group consisting of hydrogen, hydrocarbyl, and substituted hydrocarbyl;

M is any metal; and $R_2$ and $R_3$ together and $R_5$ and $R_6$ together can optionally form a ring.

An alternative route to compounds of formula V and other compounds is the synthetic sequence shown in Scheme 7.

Scheme 7

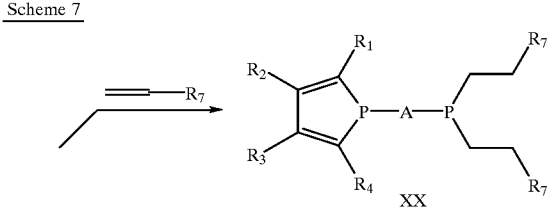

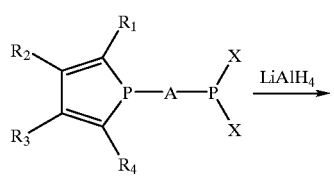

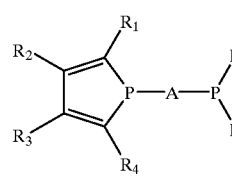

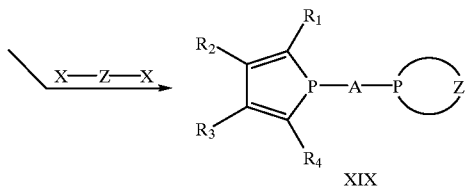

XIX

Alternate syntheses can be used to prepare bis(phosphole) compounds of formulae II from compounds previously detailed above (Scheme 8).

Figure 8

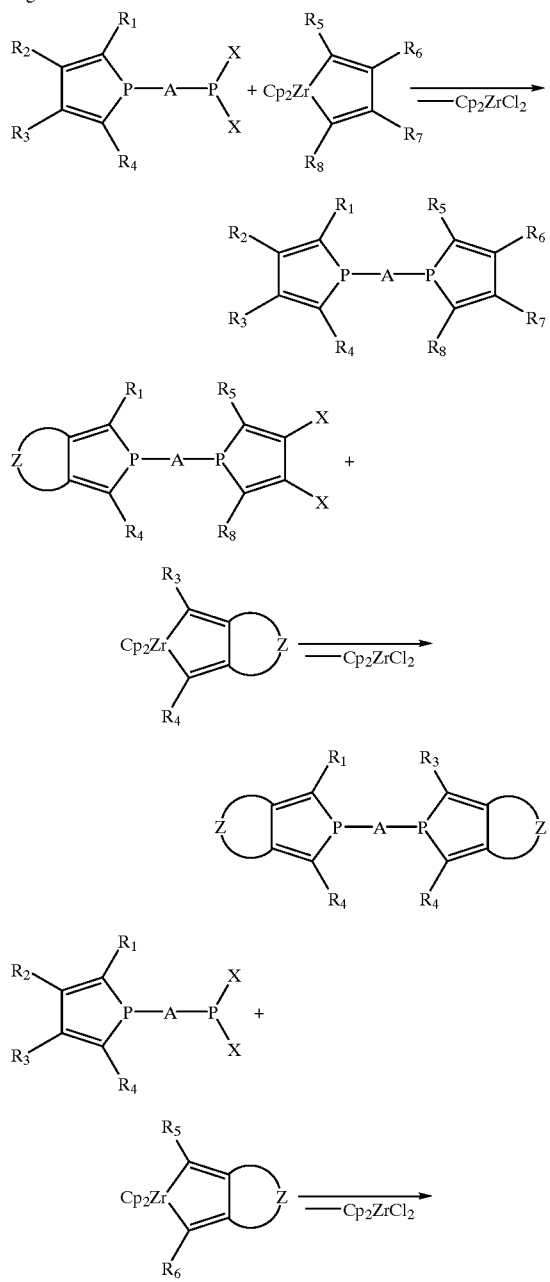

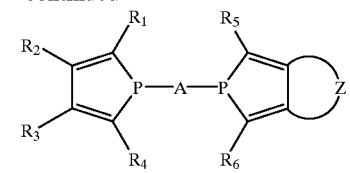

Another aspect of the present invention provides for novel coordination compounds comprising one or more transition metals complexed to one or more compounds of formulae V or II

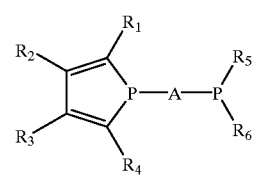

wherein $R_1$, $R_2$, $R_3$, and $R_4$ are independently selected from the group consisting of hydrogen, hydrocarbyl, and substituted hydrocarbyl;

$R_5$ and $R_6$ are independently selected from the group consisting of hydrogen, hydrocarbyl, substituted hydrocarbyl, Cl, Br, I, N, O and S;

$R_2$ and $R_3$ together and $R_5$ and $R_6$ together can optionally form a ring;

A is a divalent group consisting of optionally-substituted chains of from 1 to 12 linear, branched, or cyclic carbons, optionally containing one or more heteroatoms or organometallic groups in the chain, and —N($R_7$)—N($R_8$)—; and $R_7$ and $R_8$ are independently selected from the group consisting of hydrogen, hydrocarbyl, and substituted hydrocarbyl.

The transition metals are hereby defined as metals of atomic weight 21 through 83. Preferred metals are those of Cu(I) or of Periodic Group VIII, hereby defined as Fe, Co, Ni, Ru, Rh, Pd, Os, Ir, and Pt. Most preferred is Pd.

Reactions to form coordination compounds use either a well-defined palladium catalyst such as [(diphosphole)PdMe ($CH_3CN$)]$SbF_6$ or catalysts generated in situ by mixing the diphospole ligand with palladium salts such as [Pd($CH_3CN$)$_4$]($BF_4$)$_2$ or Pd(OAc)$_2$. Catalysts prepared in situ were made from 1,2-bis(2,3,4,5-tetramethylphospholyl)ethane and Pd(OAc)$_2$ and from 1,3-bis(2,3,4,5-tetraethylphospholyl)propane and [Pd($CH_3CN$)$_4$($BF_4$)$_2$. Preferred coordination compounds are [1,2-bis(2,3,4,5-tetramethylphospholyl)ethane]PdMeCl; {[1,2-bis(2,3,4,5-tetramethylphospholyl)ethane]PdMe($CH_3CN$)}$SbF_6$; [1,2-bis(2,3,4,5-tetramethylphospholyl)-1,2-dimethylhydrazine]PdMeCl; and {[1,2-bis(2,3,4,5-tetramethylphospholyl)-1,2-dimethylhydrazine]PdMe($CH_3CN$)}$SbF_6$.

Coordination compounds made in the instant invention can be used as catalysts for olefin/carbon monoxide polymerizations. The olefin can be an alkene or a cycloalkene containing 2–30, preferably 2–12, carbon atoms. Examples of suitable alkenes can include ethylene, propylene, any isomeric butene, pentene, hexene, octene, and dodecene, cyclooctene, cyclododecene, styrene, methylstryene, acyrlic acid, methacrylic acid, alkyl esters of acrylic and metacylic acids, and dialkenes in which the two unsaturated groups are not conjugated.

Any suitable method to prepare polymer from carbon monoxide and an olefin using the instant catalysts can be used. The catalysts themselves can be isolated before polymerization or generated in situ. Preferred catalysts for this process contain Pd.

The ligands made in the instant invention can also be used to prepare Cu(I) coordination compounds, which are useful as catalysts in ATRP (atom transfer radical polymerization) processes, as defined above, to polymerize acrylic monomers. The acrylic monomers are of the formula

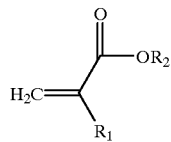

VI where $R_1$ is hydrogen, alkyl, or substituted alkyl group, and $R_2$ is hydrogen, hydrocarbyl or substituted hydrocarbyl. Preferred are compounds where $R_1$ is hydrogen, methyl or ethyl and $R_2$ is hydrogen or methyl. Most preferred is where $R_1$ and $R_2$ are both methyl (methylmethacrylate).

Any suitable method to prepare the acrylic polymers using the instant catalysts can be used. The catalysts themselves can be isolated before polymerization or generated in situ. Preferred catalysts are those formed in situ from 1,2-bis(2,3,4,5-tetramethylphospholyl)-ethane and CuCl.

Materials and Methods

The following non-limiting Examples are meant to illustrate the invention but are not intended to limit it in any way.

Abbreviations used hereafter are listed and defined below as follows:

DSC—Differential scanning calorimetry
GPC—Gel Permeation chromatography
HFIP—1,1,1,3,3,3-Hexafluoroisopropanol
COD—1,5-Cyclooctadiene
FID—Flame ionization detection
ATRP—Atom transfer radical polymerization
MMA—Methyl methacrylate
ECO—Ethylene/carbon monoxide All manipulations of air-sensitive materials were carried out with rigorous exclusion of oxygen and moisture in flame-dried Schlenk-type glassware on a dual manifold Schlenk line, interfaced to a high-vacuum ($10^{-4}$–$10^{-5}$ Torr) line, or in a nitrogen-filled Vacuum Atmospheres glovebox with a high-capacity recirculator (1–2 ppm of $O_2$). Before use, all solvents were distilled under dry nitrogen over appropriate drying agents (sodium benzophenone ketyl, metal hydrides except for chlorinated solvents). Deuterium oxide and chloroform-d were purchased from Cambridge Isotopes (Andover, Mass.). All organic starting materials were purchased from Aldrich Chemical Co., Farchan Laboratories Inc. (Kennett Square, Pa.), or Lancaster Synthesis Inc. (Windham, N.H.), and when appropriate were distilled prior to use. The substrate zirconium metallacycle ($\eta^5$—$C_5H_5$)$_2$ZrC$_4$Me$_4$, 2,3,4,5-tetramethylphospholylchloride were synthesized according to literature procedures. The substrates zirconium metallacycles ($\eta^5$—$C_5H_5$)$_2$ZrC$_4$Et$_4$, ($\eta^5$—$C_5H_5$)$_2$Zr(Me$_3$C—CCCH$_2$CH$_2$CH$_2$CC—CMe$_3$), and, 2,3,4,5-tetraethylphospholylchloride, 1,7-ditertbutyl-1,6-bicyclo[3,3]heptadiynyl-phospholylchloride were synthesized via modifications of literature methods as described below.

Physical and Analytical Measurements

NMR spectra were recorded on either a Nicolet NMC-300 wide-bore (FT, 300 MHz, $^1$H; 75 MHz, $^{13}$C, 121 MHz $^{31}$P), or GE QM-300 narrow-bore (FT, 300 MHz, $^1$H) instrument. Chemical shifts ($\delta$) for $^1$H, $^{13}$C are referenced to internal solvent resonances and reported relative to SiMe$_4$. $^{31}$P NMR shifts are reported relative to external phosphoric acid. Analytical gas chromatography was performed on a Varian Model 3700 gas chromatograph with FID detectors and a Hewlett-Packard 3390A digital recorder/integrator using a 0.125 in. i.d. column with 3.8% w/w SE-30 liquid phase on Chromosorb W support. GC/MS studies were conducted on a VG 70-250 SE instrument with 70 eV electron impact ionization. Melting points and boiling points are uncorrected.

EXAMPLES

The following Examples are meant to illustrate embodiments of the invention, but are not intended to limit its scope to the named elements.

Example 1

Synthesis of 1,2-bis(2,3,4,5-tetramethylphospholyl)ethane

Method A

A solution of Cp$_2$ZrC$_4$Me$_4$ (2.76 g, 8.47 mmol) in CH$_2$Cl$_2$ (60 mL) was added dropwise to a stirring solution of 1,2-bis(dichlorophosphino)ethane (0.97 g, 4.2 mmol) in CH$_2$Cl$_2$ (10 mL) at room temperature over a period of 10 min, and the resulting reaction mixture was stirred for an additional 10 min before removal of the solvent under vacuum. The residue was extracted with pentane (3×70 mL) and filtered. The filtrate was dried under vacuum, and then sublimated at 130° C./10$^4$ Torr to afford 1.0 g (78% yield) of (C$_4$Me$_4$P)CH$_2$CH$_2$(PC$_4$Me$_4$).

$^1$H NMR (300 MHz, CD$_2$Cl$_2$): $\delta$ 1.94 (s, 12H, 4Me), 1.91 (s, 12H, 4Me), 1.33 (s, 4H, 2CH$_2$). $^{13}$C NMR (75 MHz, CD$_2$Cl$_2$): $\delta$ 143.8 (d, Jp-c=9.8 Hz), 133.2 (s), 17.0 (d, Jp-c=23.0 Hz), 14.0 (s), 13.1 (d, Jp-c=21.8 Hz). $^{31}$P NMR (122 MHz, CD$_2$Cl$_2$): $\delta$ 16.1 (s). Anal. Calcd for C$_{18}$H$_{28}$P$_2$: C, 70.57; H, 9.21; P, 20.22. Found: C, 70.58; H, 9.02; P, 20.23.

Example 2

Method B

A mixture of $Cp_2ZrCl_2$ (27.0 g, 92.5 mmol) and 2-butyne (16.0 mL, 204 mmol) in THF (150 mL) was treated dropwise with n-butyllithium (186 mmol, 1.6 M solution in hexane) at 31 78° C. for 10 min. The resulting reaction suspension was then allowed to stir at room temperature for 2.5 hr before cooling to 78° C. 1,2-bis(dichlorophosphino) ethane (10.7 g, 46.3 mmol) was added, the mixture was warmed to room temperature and stirred for 30 min before removal of the solvent under vacuum. The residue was extracted with pentane (3×100 mL) and filtered. The filtrate was dried under vacuum, and then sublimated at 130° C./10$^4$ Torr to afford 9.9 g (70% yield) of $(C_4Me_4P)CH_2CH_2(PC_4Me_4)$.

Example 3

Synthesis of 1,2-bis(2,3,4,5-tetraethylphospholyl) ethane

A procedure similar to that described above for 1,2-bis (2,3,4,5-tetramethylphospholyl)ethane (Method A) above was used in synthesis of the title compound yielding 5.0 g (92% yield).

$^1$H NMR (300 MHz, $C_6D_6$): δ 2.53 (m, 4H), 2.27 (m, 12H), 1.65 (t, J=5.7 Hz, 4H), 1.18 (t, J=7.2 Hz, 12H), 0.99 (t, J=7.5 Hz, 12H). $^{13}$C NMR (75 MHz, $C_6D_6$): δ 148.7, 142.1, 22.0 (d, Jp-c=19.4 Hz), 21.0, 17.8 (d, Jp-c=25.5 Hz), 17.1 (d, Jp-c=8.5 Hz), 15.4. $^{31}$P NMR (122 MHz, $C_6D_6$): δ 4 (s). MS (rel. abundance): M$^+$(33), M$^+$-Me(60), M$^+$-Et(15), 223.2(6), 195.1(26), 167.1(14). High-resolution mass spectrum: Calcd for $C_{26}H_{44}P_2$ (M$^+$): 418.2918. Found: 418.2924. Anal. Calcd for $C_{26}H_{44}P_2$: C, 70.57; H, 9.21; P, 20.22. Found: C, 74.14; H, 10.70; P, XX.

Example 4

The procedure was the same as described above for 1,2-bis(2,3,4,5-tetramethylphospholyl)ethane (Method B). The product, $(C_4Et_4P)CH_2CH_2(PC_4Et_4)$, was isolated in 65% yield.

Example 5

Synthesis of 1,2-bis(2,3,4,5-tetramethylphospholyl)-1,2-dimethylhydrazine

A solution of $Cp_2ZrCl_2$ (6.67 g, 20.0 mmol) and $Cl_2PN(Me)N(Me)PCl_2$ (2.3 g, 8.6 mmol) in $CH_2Cl_2$ (150 mL) was refluxed overnight before removal of the solvent. The resulting residue was extracted with 3×100 mL of hexane. After removal of the hexane, the residue was sublimated at 170° C./10$^{-5}$ Torr, and then recrystallized from hexane to afford 2.67 g (92% yield) of title compound.

$^1$H NMR (300 MHz, $CD_2Cl_2$): δ 2.60 (d, $J_{P-H}$=3.9 Hz, 6H, 2Me-N), 2.00 (d, $J_{P-H}$=9.9 Hz, 12H, 4Me), 1.84 (d, $J_{P-H}$=2.7 Hz, 12H, 4Me). $^{13}$C NMR (75 MHz, $CD_2Cl_2$): δ 140.2 (d, Jp-c=15.9 Hz), 132.4 (s), 39.4 (s), 13.1 (s), 12.8 (d, Jp-c=3.6 Hz). $^{31}$P NMR (122 MHz, $CD_2Cl_2$): δ 77.2 (s). MS (rel. abundance): M$^+$(61), M$^+$-Me(2), 278.1(15), 197.1(31), 168.1(100), 139.1 (62). High-resolution mass spectrum: Calcd for $C_{18}H_{30}N_2P_2$(M$^+$): 336.1884. Found: 336.1881.

Example 6

Synthesis of 1,1-bis(2,3,4,5-tetramethylphospholyl) methane

A procedure similar to that described above for 1,2-bis (2,3,4,5-tetramethylphospholyl)ethane (Method A) was used in synthesis of the title compound yielding 1.30 g (97% yield).

$^1$H NMR (300 MHz, $C_6D_6$): δ 2.06 (m, 14H), 1.74 (s, 12H). $^{13}$C NMR (125.7 MHz, $C_6D_6$): δ 142.8, 136.7, 19.3 (t, Jp-c=31.9 Hz), 14.1, 14.0 (t, Jp-c=12.9 Hz). $^{31}$P NMR (122 MHz, $C_6D_6$): δ 4.3. MS (rel. abundance): M$^+$(96), M$^{30}$+H(100), M$^+$-H(30), 153(54). High-resolution mass spectrum: Calcd for $C_{17}H_{26}P_2$ (M$^+$): 292.1510. Found: 292.1513.

Example 7

Synthesis of 1,1-bis(2,3,4,5-tetraethylphospholyl) methane

A procedure similar to that described above for 1,2-bis (2,3,4,5-tetramethylphospholyl)ethane (Method A) above was used in synthesis of the title compound (1.70 g, 92% yield).

$^1$H NMR (300 MHz, $C_6D_6$): δ 1.02 (t, J=7.6 Hz, 12H), 1.25 (t, J=7.5 Hz, 12H), 2.29 (m, 8H), 2.56 (m, 10H). $^{13}$C NMR (125.7 MHz, $C_6D_6$): δ 149.0, 147.5, 23.8 (t, Jp-c=10.8 Hz), 22.7, 19.5, 17.1. $^{31}$P NMR (122 MHz, $C_6D_6$): δ -8.1. MS (rel. abundance): M$^+$(33), M$^+$-H(7), M$^+$-Me(7), M$^+$-Et (17), 209.1(100), 195.1(22), 181.1(19), 167.198). High-resolution mass spectrum: Calcd for $C_{25}H_{42}P_2$ (M$^+$): 404.2762. Found: 404.2777.

Example 8

Synthesis of 1-(2,3,4,5-tetramethylphospholyl)-2-dichlorophospinoethane

A solution of $Cl_2PCH_2CH_2PCl_2$ (4.0 g, 16.9 mmol) in $CH_2Cl_2$ (70 mL) was treated dropwise with a solution of $Cp_2ZrC_4Me_4$ (5.6 g, 16.9 mmol) in $CH_2Cl_2$ (50 mL) at −39° C. over a period of 3 hr. The resulting reaction mixture was then slowly warmed to room temperature and stirred overnight before removal of the solvent. The residues were extracted with hexane (3×100 mL) and the extracts were concentrated to give 4.1 g (90% yield) of colorless oil.

$^1$H NMR (300 MHz, $C_6D_6$): δ 1.90 (m, 2H), 1.79 (d, J=10.5 Hz, 6H), 1.63 (s, 6H), 1.59 (m, 2H). $^{13}$C NMR (75 MHz, $C_6D_6$): δ 144.8, 133.0, 37.7 (d, Jp-c=48.8 Hz), 15.2 (dd, J=9.8 Hz), 13.9, 13.0 (d, J=22.0 Hz). $^{31}$P NMR (122 MHz, $C_6D_6$): δ 197.7, 11.4. MS (rel. abundance): M$^+$(18), 232.0(100), 204.0(30), 138.0(82), 123.0(40), 91.1(26). High-resolution mass spectrum: Calcd for $C_{10}H_{16}Cl_2P_2$ (M$^+$): 268.0104. Found: 268.0101.

Example 9

Synthesis of 1-(2,3,4,5-tetramethylphospholyl)-2-dichlorophospino-1,2-dimethylhydrazine A procedure analogous to that described above for 1-(2, 3,4,5-tetramethylphospholyl)-2-dichlorophospinoethane was used in the synthesis of this diphosphine derivative with $Cp_2ZrC_4Me_4$ (6.2 g, 18.78 mmol) and $Cl_2PN(Me)N(Me)PCl_2$ (5.0 g, 18.7 mmol) at room temperature. The NMR yield (~90%) was estimated by the $^1$H and $^{31}$P NMR.

$^1$H NMR (300 MHz, $CD_2Cl_2$): δ 3.07 (d, $J_{P-H}$=5.1 Hz, 3H, Me-NPCl$_2$), 2.65 (dd, $J_{P-H}$=1.5 Hz, 3H, MeNNPCl$_2$), 2.00 (d, $J_{P-H}$=10.5 Hz, 6H, 2Me), 1.85 (d, $J_{P-H}$=3.3 Hz, 6H, 2Me). $^{13}$C NMR (75 MHz, $CD_2Cl_2$): δ 143.4 (d, Jp-c=16.9 Hz), 131.2 (s), 39.7 (s), 33.7 (d, Jp-c=6.1 Hz), 13.9 (d, Jp-c=2.4 Hz), 13.0 (d, Jp-c=21.8 Hz). $^{31}$P NMR (122 MHz, $CD_2Cl_2$): δ 153.3 (d, Jp-p=12.8 Hz), 82.9 (d, Jp-p=14.9 Hz). MS (rel. abundance): M$^+$-HCl(24), 227.1(29), 196.0(20), 167.1(90), 137.0(94), 60.0(100), 232.0(100), 204.0(30), 138.0(82), 123.0(40), 91.1(26). High-resolution mass spectrum: Calcd for $C_{10}H_{17}N_2P_2Cl$ (M$^+$-HCl): 262.0556. Found: 262.0558.

Example 10

Synthesis of 1,3-bis(2,3,4,5-tetraethylphospholyl)propane

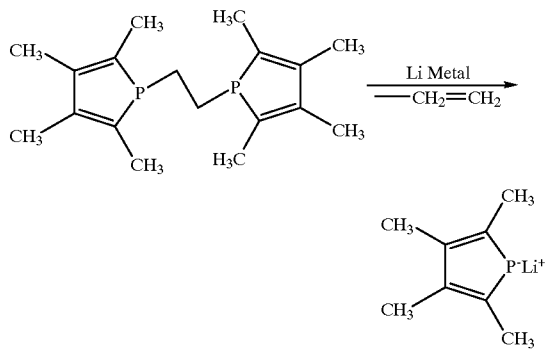

Synthesis of (2,3,4,5-tetramethylphospholyl)lithium

To a solution of 1,2-bis(2,3,4,5-tetramethylphospholyl)ethane prepared as described in Example 1, Method A, 5.0 g (16.3 mmol) in THF (70 mL) at room temperature was added clean Li ribbon (1.0 g, 144.0 mmol) under Ar. The reaction mixture was allowed to stir overnight before filtering out the excess Li. The filtrate was dried in vacuum to afford 4.7 g (99% yield) of title compound. Reduction of the ethano-bridged diphosphole ligand resulted in removal of the bridge (presumably as ethylene) and formation of the tetramethylphospholyl anion. The NMR data agree with literature data (Douglas et al., 1989, *Angew. Chem. Int. Ed. Engl.* 28 (10), 1367–7.)

Synthesis of (2,3,4,5-tetraethylphospholyl)lithium

A procedure similar to that for (2,3,4,5-tetramethylphospholyl)lithium described above was used in synthesis of the title compound using 1,1-bis(2,3,4,5-tetraethylphospholyl)methane from Example 7 as the starting material (1.23 g, 98% yield).

$^1$H NMR (300 MHz, THF-$d_8$): δ 2.54 (t, J=7.9 Hz, 4H), 2.37 (d, J=7.2 Hz, 4H), 1.14 (m, 6H), 0.96 (m, 6H). $^{31}$P NMR (122 MHz, THF-$d_8$): δ 56.0.

A suspension of Li C$_4$Et$_4$P (1.75 g, 8.67 mmol) in THF (80 mL) was treated dropwise with BrCH$_2$CH$_2$CH$_2$Br (0.88 g, 4.34 mmol) at −30° C. for 10 min. The resulting reaction mixture was then warmed to room temperature and refluxed overnight. The solution was cooled to room temperature and quenched with CH$_3$OH (3.0 mL). After removal of the solvents, the residue was extracted with 3×50 mL of hexane. The combined hexane extracts were dried under reduced pressure to give 0.81 g (44% yield) of (C$_4$Et$_4$P)CH$_2$CH$_2$CH$_2$(PC$_4$Et$_4$).

$^1$H NMR (300 MHz, C$_6$D$_6$): δ 2.50 (m, 4H), 2.25 (m, 14H), 1.68 (m, 4H), 1.19 (t, J=7.2 Hz, 12H), 0.99 (t, J=7.2 Hz, 12H). $^{13}$C NMR (75 MHz, C$_6$D$_6$): δ 147.9, 142.9, 25.4 (d, Jp-c=17.1 Hz), 22.0 (d, Jp-c=18.3 Hz), 21.5, 21.1, 17.4, 15.6. $^{31}$P NMR (122 MHz, C$_6$D$_6$): δ 2.38. MS (rel. abundance): M$^+$(17), M$^+$-Et(100), 237.2(60). High resolution mass spectrum: Calcd for C$_{27}$H$_{46}$P$_2$ (M$^+$): 432.3075. Found: 432.3094.

Examples 11–40

Reaction With Grignards

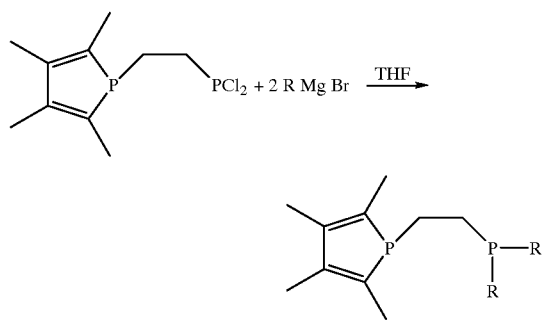

A set of twenty-eight 5 ml vials were charged with 0.25 mmol each of the following Grignards (Table 1) and 1.0 ml solution of 3 (0.1 mmol) in THF. The reactions were shaken overnight, and solvent was removed in vacuo. Samples were checked by mass spectroscopy (Atmospheric Pressure Chemical Ionization) for the presence of the expected product. In all cases, the product was observed.

TABLE 1

| Example | Grignard | Concentration | Formula | m/e +1 expected | m/e +1 found |
|---|---|---|---|---|---|
| 11 | p-CH$_3$—C$_6$H$_4$MgBr | 1.0 M/Ether | C$_{24}$H$_{30}$P$_2$ | 381.18 | 381.27 |
| 12 | p-Cl—C$_6$H$_4$MgBr | 1.0 M/Ether | C$_{22}$H$_{24}$P$_2$Cl$_2$ | 421.07 | 421.19 |
| 13 | p-(CH$_3$)$_3$C—C$_6$H$_4$MgBr | 2.0 M/Ether | C$_{30}$H$_{42}$P$_2$ | 465.28 | 465.3 |
| 14 | H—C≡C—MgBr | 0.5 M/THF | C$_{14}$H$_{18}$P$_2$ | 249.08 | 249.15 |
| 15 | CH$_3$C≡CMgBr | 0.5 M/THF | C$_{16}$H$_{22}$P$_2$ | 277.11 | 277.2 |
| 16 | p-F—C$_6$H$_4$MgBr | 2.0 M/Ether | C$_{22}$H$_{24}$P$_2$F$_2$ | 389.13 | 389.23 |
| 17 | C$_6$H$_5$C≡CMgBr | 1.0 M/THF | C$_{26}$H$_{26}$P$_2$ | 401.15 | 401.27 |
| 18 | CH$_2$=CHMgBr | 1.0 M/THF | C$_{14}$H$_{22}$P$_2$ | 253.12 | 253.17 |
| 19 | cyclopentylMgBr | 2.0 M/Ether | C$_{20}$H$_{34}$P$_2$ | 337.21 | 337.31 |
| 20 | CH$_3$(CH$_2$)$_9$MgBr | 1.0 M/Ether | C$_{30}$H$_{58}$P$_2$ | 481.40 | 481.57 |
| 21 | 4-fluoro-3-CH$_3$—C$_6$H$_3$MgBr | 1.0 M/THF | C$_{24}$H$_{28}$P$_2$F$_2$ | 417.16 | 417.27 |
| 22 | 3,4-difluoro-C$_6$H$_3$MgBr | 0.5 M/THF | C$_{22}$H$_{22}$P$_2$F$_4$ | 425.11 | 425.23 |
| 23 | p-CH$_3$(CH$_2$)$_3$C$_6$H$_4$MgBr | 0.5 M/THF | C$_{30}$H$_{42}$P$_2$ | 465.28 | 465.19 |
| 24 | 3-fluoro-2-methyl-C$_6$H$_3$MgBr | 0.5 M/THF | C$_{24}$H$_{28}$P$_2$F$_2$ | 417.16 | 417.28 |
| 25 | 2-naphthylMgBr | 0.25 M/THF | C$_{30}$H$_{30}$P$_2$ | 453.18 | 453.31 |

TABLE 1-continued

| Example | Grignard | Concentration | Formula | m/e +1 expected | m/e +1 found |
|---|---|---|---|---|---|
| 26 | p-CH$_3$S—C$_6$H$_4$MgBr | 0.5 M/THF | C$_{24}$H$_{30}$P$_2$S$_2$ | 445.13 | 445.25 |
| 27 | 3-methoxy-C$_6$H$_4$MgBr | 0.5 M/THF | C$_{24}$H$_{30}$P$_2$O$_2$ | 413.17 | 413.34 |
| 28 | 3-fluoro-4-methyl-C$_6$H$_3$MgBr | 0.5 M/THF | C$_{24}$H$_{28}$P$_2$F$_2$ | 417.16 | 417.3 |
| 29 | 2-methoxy-C$_6$H$_4$MgBr | 0.5 M/THF | C$_{24}$H$_{30}$P$_2$O$_2$ | 413.17 | 413.27 |
| 30 | 4-methoxy-C$_6$H$_4$MgBr | 0.5 M/THF | C$_{24}$H$_{30}$P$_2$O$_2$ | 413.17 | 413.32 |
| 31 | C$_6$H$_5$—O—C$_6$H$_4$MgBr | 0.5 M/THF | C$_{34}$H$_{34}$P$_2$O$_2$ | 537.20 | 537.67 |
| 32 | p-(CH$_3$)$_2$NC$_6$H$_4$MgBr | 0.5 M/THF | C$_{26}$H$_{36}$P$_2$N$_2$ | 439.23 | 439.37 |
| 33 | 2,4-difluoro-C$_6$H$_3$MgBr | 0.5 M/THF | C$_{22}$H$_{22}$P$_2$F$_4$ | 425.11 | 425.24 |
| 34 | 2,4,6-trimethyl-C$_6$H$_2$MgBr | 1.0 M/THF | C$_{28}$H$_{38}$P$_2$ | 437.24 | 437.41 |
| 35 | H$_2$C═C(CH$_3$)MgBr | 0.5 M/THF | C$_{16}$H$_{26}$P$_2$ | 281.15 | 281.21 |
| 38 | CH$_2$═CHCH$_2$MgCl | 1.0 M/Ether | C$_{16}$H$_{26}$P$_2$ | 281.15 | 281.23 |
| 39 | (CH$_3$)$_3$SiCH$_2$MgCl | 1.0 M/Ether | C$_{18}$H$_{38}$P$_2$Si$_2$ | 373.20 | 373.31 |
| 40 | R,,,,,,,T O(CH$_2$)$_3$O—CH(CH$_2$)$_2$MgBr | 0.5 M/THF | C$_{22}$H$_{38}$P$_2$O$_4$ | 429.22 | 429.29 |

Example 41

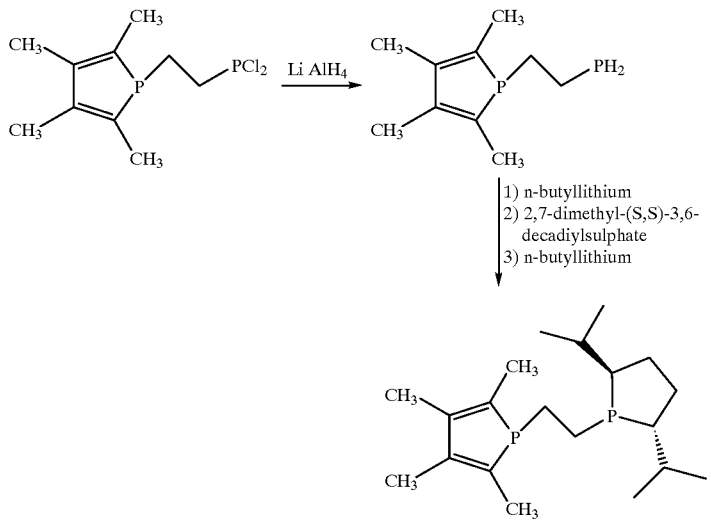

A flask was charged with 4.00 g (14.9 mmol) of [2-(tetramethylphospholyl)ethyl]dichlorophosphine and ca. 30 mL of tetrahydrofuran and was cooled to −30° C. To this was added dropwise 15 mL of a 1.0 M solution of lithium aluminum hydride in diethyl ether. After warming to room temperature, tetrahydrofuran was removed in vacuo, and the product was extracted with hexane and filtered. Removal of hexane in vacuo produced the oily compound [2-(tetramethylphosphoyl)ethyl]phosphine. $^{31}$P NMR (122 MHz, tetrahydrofuran-d$_8$): δ 17 (s), −128 (t, J$_{(P-H)}$=190 Hz). This crude product was not purified further. In another flask, 1.30 g of this product (6.49 mmol) was dissolved in 80 mL of tetrahydrofuran, and 5.1 mL of 1.6 M n-butyllithium (8.2 mmol) was added to the flask at room temperature and this was stirred for one hour. To this was added dropwise 1.50 g of 2,7-dimethyl-(R,R)-3,6-decadiylsulfate dissolved in 8 mL of THF. This was stirred for 1.5 h at room temperature. Then, 5.1 mL of 1.6 M n-butyllithium (8.2 mmol) was added to the flask at room temperature and this was stirred for one hour. The reaction mixture was quenched with 3 mL of methanol, and the solvent was removed in vacuo. The product was extracted with 150 mL of pentane, and was filtered. Removal of pentane in vacuo yielded 1.74 g of [2-(tetramethylphospholyl)ethyl]-[(R,R)-2,7-dimethyl-3,6-decadiyl]phosphine which was purified by oil sublimation (160° C., ca. 1 torr). $^{31}$P{$^1$H} NMR (122 MHz, C$_6$D$_6$): δ 18 (s), −9 (s).

Example 42

Olefin/Carbon Monoxide Copolymerization Using Diphosphole Coordinated Palladium Catalysts
Synthesis of [1,2-bis(2,3,4,5-tetramethylphospholyl)ethane]PdMeCl The solution of 1,2-bis(2,3,4,5-tetramethylphospholyl)ethane (1.538 g, 5.019 mmol) and (COD)PdMeCl(1.267 g, 4.780 mmol) in 60 mL CH$_2$Cl$_2$ was allowed to stir for 1.5 hr at RT. The mixture was filtered. The filtrate was concentrated to ca. 10 mL, followed by addition of 160 mL pentane. The solid was filtered, washed with 3×10 mL pentane and dried in vacuo. Milky white product (2.128 g, 96%) was obtained. $^1$H NMR(CD$_2$Cl$_2$): δ 0.27(dd, 3H, Pd—CH$_3$); 1.80–2.14 (m, 28H, overlapped ligand CH$_2$'s and CH$_3$'s). $^{31}$P NMR(CD$_2$Cl$_2$): δ 59.63, 73.55 (1P each).

Example 43

Synthesis of {[1,2-bis(2,3,4,5-tetramethylphospholyl)ethane]PdMe(CH$_3$CN)}SbF$_6$ To a −30° C. solution of [1,2-bis(2,3,4,5-tetramethylphospholyl)ethane]PdMeCl (1.47 g, 3.17 mmol)

and $CH_3CN$ (1.30 g, 31.7 mmol) in 50 mL $CH_2Cl_2$ was added $AgSbF_6$ (1.090 g, 3.17 mmol). This was allowed to warm up slowly to RT and stir at RT for 30 min. The mixture was filtered. The filtrate was concentrated to ca. 5 mL. To the concentrated solution was added 80 mL pentane. The solid was filtered, washed with 3×10 mL pentane and dried in vacuo. Yellow solid (2.172 g, 97%) was obtained. $^1$H NMR($CD_2Cl_2$): δ 0.29(dd, 3H, Pd—$CH_3$); 1.80–2.20 (m, 28H, overlapped ligand $CH_2$'s and $CH_3$'s); 2.24(s, 3H $CH_3CN$). $^{31}$P NMR($CD_2Cl_2$): δ 60.62, 73.32(d, J=18.0 Hz, 1P each).

Example 44

Synthesis of [1,2-bis(2,3,4,5-tetramethylphospholyl)-1,2-dimethylhydrazine] PdMeCl The solution of 1,2-bis(2,3,4,5-tetramethylphospholyl)-1,2-dimethylhydrazine (0.341 g, 1.01 mmol) and (COD) PdMeCl (0.224 g, 0.845 mmol) in 20 mL $CH_2Cl_2$ was allowed to stir for 1.5 hr at RT. The mixture was filtered. The filtrate was concentrated to ca. 5 mL, followed by addition of 75 mL pentane. The solid was filtered, washed with 3×5 mL pentane and dried in vacuo. Red brown product (0.253 g, 61%) was obtained. $^1$H NMR($CD_2Cl_2$): δ 0.25 (dd, 3H, Pd—$CH_3$); 1.98 (s, 12H, 3,4-$CH_3$'s); 2.01 (dd, 12H, 2,5-$CH_3$'s); 2.56 (d, J=8.4 Hz, 3H, N—$CH_3$); 2.64 (d, J=10.2 Hz, 3H, N—$CH'_3$). $^{31}$P NMR($CD_2Cl_2$): δ 115.80 (d, J=30.3 Hz, 1P); 127.40 (d, J=28.9 Hz, 1P).

Example 45

Synthesis of {[1,2-bis(2,3,4,5-tetramethylphospholyl)-1,2-dimethylhydrazine] PdMe($CH_3CN$)}$SbF_6$ To a −30° C. solution of [1,2-bis(2,3,4,5-tetramethylphospholyl)-1,2-dimethylhydrazine]PdMeCl (0.20 g, 0.406 mmol) and $CH_3CN$ (0.17 g, 4.15 mmol) in 20 mL $CH_2Cl_2$ was added $AgSbF_6$(0.1394 g, 0.406 mmol). This was allowed to warm up slowly to RT and stir at RT for 40 min. The mixture was filtered through Celite® filteration aid. The filtrate was concentrated to ca. 5 mL. To the concentrated solution was added 75 mL pentane. The solid was filtered, washed with 2×5 mL pentane and dried in vacuo. Light brown solid (0.23 g, 77%) was obtained. $^1$H NMR($CD_2Cl_2$): δ 0.27 (dd, 3H, Pd—$CH_3$); 1.87 (s, 12H, 3,4-$CH_3$'s); 1.88 (dd, 12H, 2,5-$CH_3$'s); 2.26 (s, 3H $CH_3CN$); 2.57 (d, J=8.7 Hz, 3H, N—$CH_3$); 2.67 (d, J=11.1 Hz, 3H, N—$CH'_3$). $^{31}$P NMR($CD_2Cl_2$): δ 115.58 (d, J=28.5 Hz, 1P); 125.48 (d, J=30.3 Hz, 1P).

Polymerizations

Reactions were done by using either well-defined palladium catalysts such as [(diphosphole)PdMe($CH_3CN$)]$SbF_6$ or catalysts generated in situ by mixing the diphosphole ligand with the palladium salts such as [Pd($CH_3CN$)$_4$]($BF_4$)$_2$ or Pd(OAc)$_2$. Adding strong acid such as p-toluenesulfonic acid is important when Pd(OAc)$_2$ is used as the catalyst precursor. Adding excess of benzoquinone as the oxidant in general helps the copolymer yield. The copolymerization works in common organic solvents such as $CH_2Cl_2$, chlorobenzene and methanol. The synthesis of the organometalic complexes were carried out in a nitrogen drybox. Catalyst screening was more conveniently done in multishaker tubes. When using shaker tubes for ligand and catalyst scouting (Table 2), 25 mL-sized tubes were used. Ligand, catalyst precursor (or single-component catalyst), oxidant (sometimes also p-$CH_3C_6H_4SO_3H.H_2O$ acid) and 5 mL of specified solvent(s) were mixed in the shaker tubes. After purging with nitrogen, these tubes were pressured up with ethylene/CO (1:1) mixed gas and was shaken at 60° C. under ethylene/CO pressure for 18 hr.

Example 46

High Pressure Slurry ECO Copolymerization (100° C., 900 psi)

{[1,2-bis(2,3,4,5-tetramethylphospholyl)ethane]PdMe($CH_3CN$)}$SbF_6$ (1.00 g, 1.42 mmole), benzoquinone (3.07 g, 28.4 mmole) and 1460 mL methanol were charged into an one gallon autoclave. The reactor was then charged with mixed ethylene/carbon monoxide gas (1:1) and the temperature was raised up to 100° C. The mixture was allowed to stir at 100° C. under 900 psi of E/CO mixed gas for 6 hr. The reaction was exothermic (cooling coil was used to control the temperature by using water as coolant). Upon cooling, the polymer/methanol mixture was transferred to a blender and was blended to powders. The powdery polymer was then filtered, washed with methanol repeatedly and dried in vacuo at 100° C. for 3 days. White powdery polymer (356 g) was obtained. Based on $^1$H and $^{13}$C NMR, the polymer is perfectly alternating ethylene/CO copolymer. The copolymer exhibited a m.p. of 250° C. based on DSC. GPC (HFIP, polyethylene terephthalate standard): Mw=236,000; Mn=46,800; Mw/Mn=5.0.

Example 47

Slurry ECO Copolymerization (60° C., 700 psi)

{[1,2-bis(2,3,4,5-tetramethylphospholyl)ethane]PdMe($CH_3CN$)}$SbF_6$ (0.60 g, 0.852 mmole), benzoquinone (4.6 g, 42.6 mmole), 1000 mL methanol and 500 mL toluene were charged into an one gallon autoclave. The reactor was then charged with mixed ethylene/carbon monoxide gas (1:1) and the temperature was raised up to 60° C. The mixture was allowed to stir at 60° C. under 700 psi of ECO mixed gas for 6 hr. The reaction was exothermic (cooling coil was used to control the temperature by using water as coolant). Upon cooling, the polymer/methanol mixture was transferred to a blender and was blended to powders. The powdery polymer was then filtered, washed with methanol repeatedly and dried in vacuo at 100° C. for one day. White powdery polymer (243 g) was obtained. Based on $^1$H and $^{13}$C NMR, the polymer is perfectly alternating ethylene/CO copolymer. The copolymer exhibited a m.p. of 242° C. based on DSC. GPC (HFIP, polyethylene terephthalate standard): Mw=149,000; Mn=63,000; Mw/Mn=2.4.

Examples 48–53

Shaker Tube Screening of Ligands and Catalysts for ECO Copolymerization (60° C., 18 hr)

TABLE 1

Shaker tube experiments for Ethylene/CO copolymerization

| Ex. | Ligand (mg) | Catalyst or precursor (mg) | Benzo-quinone (mg) | Acid (mg) | Solvent | E/CO Pressure (psi) | Mw/Mn | Copolymer Yield (g) | m.p (° C.) |
|---|---|---|---|---|---|---|---|---|---|
| 48 | 0 | C-1 (4.7) | 14.4 | 0 | CH$_3$OH | 708 | na | 8.5 | na |
| 49 | 0 | C-1 (42) | 0 | 0 | CH$_3$OH | 880 | na | 23.3 | na |
| 50 | L-1 (22) | Pd (OAc)$_2$ (12.5) | 130 | 228 | CH$_3$OH/ toluene 2:1 | 800 | na | 0.5 | na |
| 51 | 0 | C-1 (2.0) | 6.3 | 0 | CH$_3$OH | 885 | 381,000/ 151,000 | 1.53 | 253 |
| 52 | 0 | C-2 (29.4) | 89.6 | 0 | CH$_3$OH | 885 | 509,000/ 218,000 | 5.0 | 245 |
| 53 | L-2 (5.5) | P-1 (5.7) | 27.6 | 0 | CH$_3$OH | 600 | 707,000/ 312,000 | 11.8 | na |

L-1 = 1,2-bis(2,3,4,5-tetramethylphospholyl)ethane
L-2 = 1,3-bis(2,3,4,5-tetraethylphospholyl)propane
C-1 = {[1,2-bis(2,3,4,5-tetramethylphospholyl)ethane]PdMe(CH$_3$CN)}SbF$_6$
C-2 = {[1,2-bis(2,3,4,5-tetramethylphospholyl)-1,2-dimethylhydrazine]PdMe(CH$_3$CN)}SbF$_6$
P-1 = [Pd(CH$_3$CN)$_4$](BF$_4$)$_2$

Example 54

ATRP of MMA using Cu(I)-diphosphole Complex as Catalyst

MMA was passed through a basic alumina column to remove inhibitor, then degassed by freeze-thaw cycle three times. 10 mg of CuCl and 62 mg of 1,2-bis(2,3,4,5-tetramethylphospholyl)ethane were put into 5.0 mL of degassed toluene. 5.0 mL of purified MMA and 66 μL of 2,2'-dichloroacetophenone were added into the above catalyst solution. The solution was mixed well in a Schlenck flask and the flask was sealed under nitrogen and then immersed in an oil bath set at 80° C. Polymerization proceeded at 80° C. with stirring for 16 hrs. After polymerization was stopped, the solution was diluted with more toluene and then polymer was precipitated into methanol. Polymer solid was collected by filtration, washed with methanol, and dried under vacuum. 0.35 g polymer was obtained (7.5% conversion of MMA). The polymer was analyzed by GPC with THF as eluent and PMMA as standard. The number average molecular weight (M$_n$) was 20200 and M$_w$/M$_n$ was 1.32.

We claim:

1. A process for preparing compounds of formulae I and II

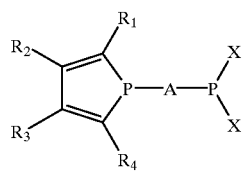

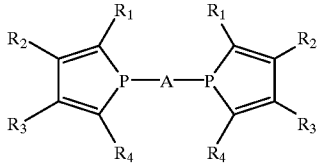

comprising reacting suitable equivalents of a compound of formula X$_2$P—A—PX$_2$ (III) with a compound of formula IV;

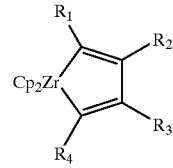

wherein
R$_1$, R$_2$, R$_3$, and R$_4$ are independently selected from the group consisting of hydrogen, hydrocarbyl, and substituted hydrocarbyl;
R$_2$ and R$_3$ together can optionally form a ring;
Cp is cyclopentadienyl;
X is selected from the group consisting of Cl, Br, and I;
A is a divalent group consisting of optionally-substituted chains of from 1 to 12 linear, branched, or cyclic carbons, optionally containing one or more heteroatoms or organometallic groups in the chain, and —N(R$_7$)—N(R$_8$)—; and
R$_7$ and R$_8$ are independently selected from the group consisting of hydrogen, hydrocarbyl, and substituted hydrocarbyl.

2. The process of claim 1 where A is selected from the group consisting of a carbon chain of 1–3 carbons and —N(R$_7$)—N(R$_8$)—, wherein R$_7$ and R$_8$ are independently selected from the group consisting of hydrogen, hydrocarbyl, and substituted hydrocarbyl.

3. The process of claim 2 where $R_1$, $R_2$, $R_3$, and $R_4$ are alkyl groups.

4. The process of claim 1 wherein the compound of formulae I or II is selected from the group consisting of 1,2-bis(2,3,4,5-tetramethylphospholyl)ethane; 1,2-bis(2,3,4,5-tetraethylphospholyl)ethane; 1,1-bis(2,3,4,5-tetramethylphospholyl)methane; 1,1-bis(2,3,4,5-tetraethylphospholyl)methane; 1,2-bis(2,3,4,5-tetramethylphospholyl)-1,2-dimethylhydrazine, 1-(2,3,4,5-tetramethylphospholyl)-2-dichlorophosphinoethane; and 1-(2,3,4,5-tetramethylphospholyl)-2-dichlorophosphinoethane-1,2-dimethylhydrazine.

* * * * *

UNITED STATES PATENT AND TRADEMARK OFFICE
CERTIFICATE OF CORRECTION

PATENT NO. : 6,137,012
DATED : October 24, 2000
INVENTOR(S) : Paul J. Fagan, George Y. Li Page 1 of 1

It is certified that error appears in the above-identified patent and that said Letters Patent is hereby corrected as shown below:

<u>Title page,</u>
Item [75] Inventors, "Paul J. Fagan; George Yanwu Li, both of Wilmington; Zhibin Guan; Lin Wang, both of Hockessin, all of Del." should read -- Paul J. Fagan; George Yanwu Li, both of Wilmington, Del. --.

Signed and Sealed this

Eighteenth Day of December, 2001

Attest:

Attesting Officer

JAMES E. ROGAN
Director of the United States Patent and Trademark Office